US 6,675,047 B1

(12) United States Patent
Konoplev et al.

(10) Patent No.: US 6,675,047 B1
(45) Date of Patent: Jan. 6, 2004

(54) ELECTROMAGNETIC-FIELD THERAPY METHOD AND DEVICE

(76) Inventors: Sergei Petrovich Konoplev, 141570 Moskovskava obl., pos. Mendeleevo, ul. Institutskava, d. 16, kv. 31, Moskovskava obl. (RU); Tatyana Petrovna Konopleva, 141570 Moskovskava obl., pos. Mendeleevo, ul. Institutskava, d. 16, kv. 31, Moskovskava obl. (RU)

(*) Notice: Subject to any disclaimer, the term of this patent is extended or adjusted under 35 U.S.C. 154(b) by 0 days.

(21) Appl. No.: 09/787,975

(22) PCT Filed: Oct. 14, 1999

(86) PCT No.: PCT/RU99/00382

§ 371 (c)(1),
(2), (4) Date: May 11, 2001

(87) PCT Pub. No.: WO01/00275

PCT Pub. Date: Jan. 4, 2001

(30) Foreign Application Priority Data

Jun. 28, 1999 (RU) .............................................. 99113012

(51) Int. Cl.[7] .................................................. A61N 1/08
(52) U.S. Cl. ............................................. 607/50; 607/155
(58) Field of Search ................................. 607/2, 156, 66, 607/68, 50, 155

(56) References Cited

U.S. PATENT DOCUMENTS 4,919,139 A * 4/1990 Brodard ........................ 607/59
5,578,060 A * 11/1996 Pohl et al. ...................... 607/3
5,584,863 A * 12/1996 Rauch et al. ................... 607/2

FOREIGN PATENT DOCUMENTS

| RU | 2093213 | 9/1991 |
| RU | 2038101 C1 | 6/1995 |
| RU | 94006958 A1 | 12/1995 |

* cited by examiner

Primary Examiner—Mark Bockelman
(74) Attorney, Agent, or Firm—J. Herbert O'Toole; Nexsen Pruet Jacobs & Pollard, LLC

(57) ABSTRACT

A method of electromagnetic field therapy consists in that an organ or a whole organism is locally acted upon with a pulsed electromagnetic field with a radio pulse packet repetition frequency within a range of from 0.1 to 100 Hz with spacing of 0.01 Hz, and the electromagnetic field carrier frequency ranging from 10 to 15 kHz. An apparatus for carrying out the method of the invention comprises a power supply source (1), a stabilizer (2), an antenna (4), a matching unit (3), a unit (5) for shaping packets of radio pulses, made as a microprocessor controller with a permanent memory, a computer interface unit (6), a liquid-crystal display (7), and a keyboard (8).

5 Claims, 1 Drawing Sheet

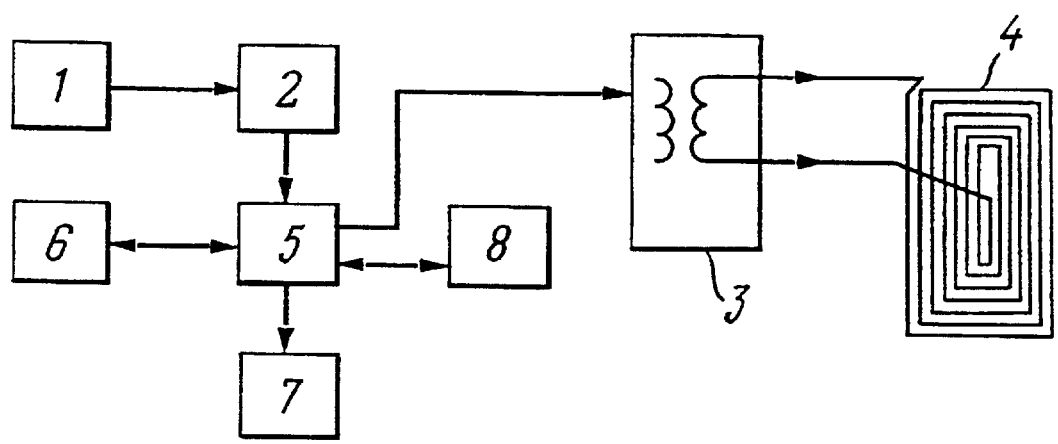

ELECTROMAGNETIC-FIELD THERAPY METHOD AND DEVICE

This application is a 371 of PCT/RU99/00382 field Oct. 14, 1999

TECHNICAL FIELD

The present invention relates to medicine and more particularly to a method of and an apparatus for electromagnetic field therapy.

BACKGROUND ART

The present invention is a logical continuation of investigations in the field of low-frequency relaxation therapy based on the action through electrodes upon biologically active points of the human body or biologically active zones of the human body with short electric pulses lasting from 0.1 ms to 100 ms and having current intensity of from 0.1 mA to 100 mA. In most cases the biologically active points coincide with classical acupuncture points accepted by various schools of traditional oriental medicine.

Known in the art are apparatus for searching for biologically active points, measuring their resistance and biologically active zones (in accordance with the Nakatani-Ryodoraku procedure, with Doctor R. Völl's techniques, etc.), and for contact action thereon with needles, electric pulses, microwave radiation, extremely-high frequency radiation, light and laser radiation of different ranges, from the ultraviolet to infrared. In addition, these apparatus are combined with each other and bear different names: electrotherapeutics, extremely-high frequency therapy, microwave therapy, transcutaneous stimulators, laser puncture, and the like.

A feature common to all the above-named apparatus is introducing into the biologically active points and zones in various form and via them a therapeutic action upon the human organism.

A method of electromagnetic field therapy is known (RU, 2132204), consisting in that the human organism is acted upon with a pulsed electromagnetic field having an intensity of 0.1 V/m$^2$ without changing the energy information homeostasis with a radio pulse packet repetition frequency within a range of from 0.2 to 10 Hz with spacing of 0.01 Hz.

However, this method fails to provide harmonization of the functioning of organs and systems because of resonance phenomena induced in the organism by the prescribed frequencies. Therefore, the possibilities of this method cannot be broadened, and the treatment process cannot be automated.

An apparatus for electromagnetic field therapy is known (RU 2132204), which comprises a power supply source connected to a stabilizer, an antenna, a matching unit coupled to the antenna, a unit for shaping packets of radio pulses whose input is connected to the stabilizer and whose output is connected to the matching unit. The unit for shaping packets of radio pulses is designed as a generator of electric pulses operating in the frequency range of from 0.2 to 10 Hz, a modulator, a frequency modulation indicator, an audio frequency generator whose output is connected though the matching unit to the antenna which is made corkscrew, a control device connected to the indicator and to the generator of electric pulses. The generator of electric pulses is coupled through the modulator to the audio frequency generator. The apparatus also comprises coverlets. A screening grid is sewn into the upper textile fabric layer of one coverlet, and an antenna made from copper wire is sewn into the other.

The apparatus operates in the following manner. An apron coverlet is placed on the chest or back of a human, the plug and socket connection is effected, the switch is set to position "on", the power supplied through the stabilizer to the generator of electric pulses in the frequency range of from 0.2 to 10 Hz, to the modulator and to the audio frequency generator. The generated oscillations modulated through the modulator from the generator of electric pulses in the frequency range of from 0.2 to 10 Hz in the form of pulse packets are fed to the matching device and come via the appropriate connector and wire to the antenna, exciting electromagnetic ultralow-intensity oscillations in the antenna circuit. These ultralow-intensity oscillations produce curative effect in the frequency range of from 0.2 to 10 Hz in accordance with Doctor R. Völl's procedure. The pulse packet repetition frequency is displayed on the indicator and selected with the help of the control device.

The present apparatus has a 5% error in setting the frequency at the edges of the range. For the therapy to be good and effective, the error in frequency setting with the quartz accuracy should not exceed 0.2%. Small organs and systems cannot be treated locally, because the effect spreads uniformly all over the organism.

With this apparatus the possibilities of the method cannot be broadened, and the treatment process cannot be automated either. This apparatus can be used for treating only various human organs, but not their functional disorders, psychic deviations connected with disturbances of the organs. This apparatus cannot ensure harmonization of the functioning of organs and systems.

DISCLOSURE OF THE INVENTION

The present invention is directed to the provision of a method of and an apparatus for the electromagnetic field therapy with such an embodiment thereof which would ensure harmonization of the functioning of human organs and systems owing to the resonance phenomena induced in the organism by prescribed frequencies, and thereby broaden the possibility of their use, the treatment process being automated.

Said problem is solved by that in a method of electromagnetic field therapy, residing in that the human organism is acted upon with a pulsed electromagnetic field having an intensity of 0.1 V/m$^2$ without changing the energy information homeostasis with a radio pulse packet repetition frequency within a range of from 0.2 to 10 Hz with spacing of 0.01 Hz, according to the invention, additionally acts upon the human organism with a pulsed electromagnetic field with a radio pulse packet repetition frequency within a range of from 0.1 to 0.2 Hz and from 10 to 100 Hz, the electromagnetic field carrier frequency ranging from 10 to 15 kHz.

The action on the human organism with the pulsed electromagnetic field can be performed locally through the projection zone of its organ.

The action with the pulsed electromagnetic field can be performed on the whole organism.

Said problem is also solved by that the apparatus for electromagnetic field therapy, comprising a power supply source connected to a stabilizer, an antenna, a matching unit coupled to the antenna, a unit for shaping packets of radio pulses whose input is connected to the stabilizer and whose output is connected to the matching unit, according to the invention, comprises a computer interface unit, a liquid-crystal display intended for displaying the parameters of the treatment program being carried out, and a control keyboard, connected to the unit for shaping packets of radio pulses, which is made as a microprocessor controller with a permanent memory with a capacity for up to 1000 programs of treatment, up to 20 frequencies in each program, each frequency lasting for 1 to 4000 seconds.

The present invention is intended for carrying out low-frequency therapy by a non-contact method.

The apparatus is designed on the basis of combining present-day world advances in the field of acting with specific frequencies on humans and a method of acting with weak electromagnetic fields. The possibility of acting on all the meridians of the human organism simultaneously without disturbing the energy-information equilibrium is of special value, since it appreciably increases the apparatus effectiveness.

Pulse field therapy produces a complex effect on the human organism, because it contributes to an improvement in the energy metabolism, increases the mobility of lymph, enhances the blood supply of capillaries, and, as a consequence, improves nutrition of all tissues of the organism. The pulse field therapy liquidates stagnation of energy in tissues, whereby painful sensations are eliminated. The pulse therapy improves ion exchange on the level of cells, regulates the intracellular pressure, this contributing to normalization of the overall metabolism.

The size of the apparatus is small enough to carry it in one's pocket. The range of its application is very wide: it can be used when riding in a car, during one's rest, when sitting for an examination, during an evening party, in extreme situations, when communicating with "tough customers", and in many other cases.

The proposed method of and apparatus for electromagnetic field therapy in such embodiment thereof made it possible to ensure harmonization of the functioning of human organs and systems owing to the resonance phenomena induced in the organism by the prescribed frequencies, and thereby to extend the potential applications of said method and apparatus and to make the process of treatment automatic.

BRIEF DESCRIPTION OF DRAWINGS

The invention will further be exemplified by a particular embodiment thereof with reference to the accompanying drawing which shows a block diagram of the proposed apparatus for the electromagnetic field therapy.

PREFERRED EMBODIMENT OF THE INVENTION

The proposed method of the electric field therapy consists in acting on the human organism with a pulsed electromagnetic field having an intensity of 0.1 V/m$^2$, with a radio pulse packet repetition frequency within a range of from 0.1 to 100 Hz with spacing of 0.01 Hz, and the electromagnetic field carrier frequency ranging from 10 to 15 kHz. The energy-information homeostasis remains unchanged. The action on the human organism with the pulsed electromagnetic field can be performed locally through the projection zone of its organ or the action with the pulsed electromagnetic field can be performed on the whole organism.

Using this method, it is possible to treat different organs and systems of the organism with a weak electromagnetic field having a frequency of from 10 to 15 kHz, modulated with a frequency within a range of from 0.1 to 100 Hz with the quantization step of 0.01 Hz, selected in accordance with the procedures of Doctors R. Völl, F. Kramer, O. Clauss, O. Kollmer, Paul-Schmidt, and orthers. This treatment is possible due to the fact that with the help of a weak electromagnetic field a resonance is induced in organs and tissues, and thereby the functions of the organism are harmonized. This, in turn, is necessary for the organs not to be forced to perform functions which are not peculiar to them.

Passive electric properties of biological tissues are characterized by an impedance, the value of which is determined by the capacitive susceptance and conductance with the corresponding conductance of the tissues. The active component of the electric conductivity at low frequencies depends, in the main, on the amount and the electrolyte composition of the intercellular liquid; at high frequencies an additional contribution is made by the electric conductivity of cells. Since the resistance of cells is series-connected with the capacity of the cellular membrane, there occurs a frequency dispersion of the electric conductivity of biological tissues. Having high dielectric property and an extremely small thickness, bilayer lipid membranes are characterized by a high specific electric capacity. A large value of the charge capacity of membranes and, consequently, the capacitance properties of biological tissues, are due to the considerable polarization capacity of the dielectric of the membrane, which depends on its relative permittivity. At high frequencies polarization mechanisms become switched-off with slowing-down of the relaxation time; therefore, with an increase in the frequency, the capacity of tissues must decrease, as in the case of an increase in the permittivity.

In the range of low frequencies the impedance of tissues is determined, mainly, by their resistive properties. To this range there pertain tissues having a high electric conductivity (nervous tissue). To the range of medium frequencies their pertain tissues whose electrical properties are determined by the resistive and capacitive properties (parenchymatous organs). In the range of high frequencies the character of the electrical properties of tissues is ca-pacitive (membranes, lipids). Slowed-down polarization mechanisms in this range of frequencies may involve considerable dielectric losses in the tissues (heating). Therefore, the living cell can be represented as an oscillatory circuit with a capacitance and a resistance, the capacitance (membrane) being determined by free-radical reactions and by the antioxidant protection system, whereas the resistance is determined by enzymatic oxidation.

An oscillatory circuit possesses such property as inductance—the ability to induce, owing to its magnetic moment, an electric current in another circuit or in a closed conductor. Generation of electromagnetic field pulses from units to tens of Hz is a characteristic feature of normal functioning of various human organs. It is not only the cell that can be represented as an oscillatory circuit, but higher organization levels of living matter as well: tissues and organs with different predominance of glucose oxidation pathways, systems of organs and the entire organism as an inductively equilibrium system of oscillatory circuits. Such an organ as the liver comprises both glucose oxidation pathways in equal proportions, which makes it the key organ in the system regulating the capacitance and inductance of the organism. The blood circulation system per se is also a stage of closed conductors, from the loops of capillaries to the greater and lesser circulation. Difference in the impedances of venous and arterial blood provides conditions for the mutual influence of organs. The electric properties of blood are determined by the amount of hemoglobin, oxygen and other cyclic compounds in it, by its protein-electrolytic composition, and by the circulation rate.

Therefore, an electric field considered within the framework of classical electrodynamics can integrate the functioning of the whole organism, by creating and preserving the specialization of different tissues. The blood circulation system is the intermediary through which regulation is effected. The energy ch'i, taught by the ancient Chinese medicine to be circulating in the blood, becomes quite real, having its physical equivalent. Acupuncture rests on the philosophy of ancient Chinese medicine which regards the organism as a single whole, in which each part is subordinated to this whole, and the whole depends on each part. The energy ch'i, divided into yang and yin principles in their constant interaction and dynamic balance, fully corresponds to the described integration on the basis of the electromagnetic field of an oscillatory circuit, wherein the ch'i is replaced by inductance and the yang and the yin are represented as a capacitor and a resistor. Then biologically active points represent additional energy regulation sources in the form of a nerve coil around a nerve core in which an electromotive force will be generated on excitation of the nerve or weaken on removal of the excitation from the nerve, and vice versa.

The electroacupuncture diagnostics according to Völl makes it possible to evaluate the degree of balance in the oscillatory circuits of different organs and tissues. The output direct current and voltage provided by the apparatus in diagnostic testing of points of the meridians do not exceed the physiological values. Thereby, we introduce into the living oscillatory circuit an electromagnetic interference which under normal conditions must not disturb its balance, and the pointer of the instrument must be in the middle of its scale. An increased inductance of the organ will give higher measurement figures, whereas a slowdown of oxidation processes will give low figures. Quadratic estimates show a predominance of the inductance of the nervous system over other tissues, since in this case they display capacitive properties compared with the resistive properties of the nervous tissue. Low resulting values are indicative of a reduction in the inductance of the nervous tissue (an imbalance in its oscillatory circuit) or of an increase, for some reason, in the inductance of blood. A drop of the instrument pointer indicates a large self-induction, i.e., runaway of the organism.

The electromagnetic oscillations which exist inside the very living organism depend only in part on the oscillations existing outside the organism. Though natural oscillations of the organism are excited by the oscillations of external magnetic fields, these natural oscillations then originate in the organism again, in a specific form. Each organ and each cell has its specific spectrum of oscillations, its specific characteristics of these oscillations (form and kind, as well as frequency). Maintenance of these oscillations depends on the "Q-factor" of the resonator of the cell, organ, tissue or organism as a whole. If the "Q-factor" of the resonator is disturbed or absent, incoherent, inadequate, pathological electromagnetic oscillations may arise. When the mechanism of self-regulation and sanitation, existing in the organism, proves to be unable to destructurate these oscillations, the result will be a disease. Specific responses of the human organism to the action of an artificial electromagnetic field were detected only when passing over to ultra-weak low-frequency intensities (when the intensities of a field induced inside the organism were essentially smaller than 0.1 V/cm$^2$). It should be noted that when the intensity of an external field is on the order of 10 V/m, the values of the field induced inside the organism practically cannot be measured experimentally. These values were obtained by calculations and amounted to from $10^{-8}$ to $10^{-7}$ V/m. The fact that the organism responds to such small field intensities does not contradict commonly adopted physical estimates based on the signal/noise ratio. Indeed, since physiological processes are controlled by ultra-low waves, i.e., by processes with passband on the order of 1 Hz, with the specific resistance of nervous tissues R≈300 Ω/cm the intensity of thermal noises is $U_\varnothing \approx 10^{-9}$ V/cm, i.e., an order of magnitude lower than the above-cited intensity values. When comparing the effects produced on humans by artificial and natural low-frequency electromagnetic fields in the range from 0.1 to 100 Hz, it should also be taken into account that the time of action of artificial electromagnetic fields is short, its duration being appreciably shorter than human life, whereas the effect of natural electromagnetic fields operates permanently throughout the life of man. In this connection, it can be expected that for obtaining a curative effect by from the action of an artificial electromagnetic field (EMF), its intensity must be higher. In order to explain the effect of low frequencies in the range of from 0.1 to 100 Hz on humans, an assumption was advanced that receptors on the electromagnetic field can be systems of meridians and acupuncture points. Since all the known hypotheses of their role were confined to an abstract theoretical consideration of their purpose, the above assumption was verified by experimental investigations directed to detecting low frequencies in the range of from 0.1 to 100 Hz in the electric signals in the zones of skin projections of the acupuncture points. Searching for such signals was carried out by proceeding from the following considerations.

In accordance with the principle of reciprocity of antennas, any structure performing reception of electromagnetic fields is also capable of radiating in the same frequency range. Therefore, the object of the investigation was to find electric signals within the range of low frequencies from 0.1 to 100 Hz in the zones of skin projections of the acupuncture points. In the course of experimental investigations, low-frequency electric signals were detected in said zones. Those signals had maximum amplitude values at some discrete frequencies in the range of from a few Hz to tens of Hz. Furthermore, weak low-frequency radiations of electromagnetic fields in the range of from 0.1 to 100 Hz, also having a discrete spectrum in the range of tens Hz, were recorded in above the body surface in these zones. It was established that as the probe is displaced from the zone of acupuncture points, the amplitudes of received signals decrease sharply; the character of the spatial distribution of the signals in their zone is anisotropic. In neutral portions of the body the character of observed signals was noise-like, and their amplitude was 5 to 10 times smaller than in the zone of acupuncture points.

The obtained experimental data can with sufficient reason be regarded as proving that the receptors sensitive to electromagnetic fields in the frequency range of from a few Hz to tens of Hz are acupuncture points and the system of meridians. Naturally, for effective reception of low frequencies in the range of from 0.1 to 100 Hz a biological object must have a sufficiently large number of receptors maximum spaced over its body. These very requirements are fulfilled in the meridian structures of acupuncture points in all living organisms. Consequently, it can be supposed that their meridian structures are systems of discrete receiving elements. Each such discrete structure is connected with one or another functional system of the organism and ensures individual reception of synchronizing low frequencies in the range of from 0.1 to 100 Hz. A large oscillation of systems with weakly suppressed natural oscillations in the case they are excited by relatively weak external forces at or near the natural frequency of the system is called resonance. The present method makes it possible to cause a resonance in organs and systems with the help of a weak electromagnetic field and thereby to harmonize functioning of the organism. This is necessary to preclude making the organs perform functions not indigenous to them. Thereby the effect of overdosage is obviated. Since diseases of the organs can be caused by different factors, for treating diseases it is necessary to actuate different systems of the organism, i.e., sets of frequencies. Therefore, a treating program must consist of a set of frequencies, each of which operates for a preset period of time, inducing a resonance in the appropriate organs and systems. Numerous experiments were carried out at central hospitals and large medical centers of Moscow for selecting the carrier frequency. Statistical data have shown that an optimal carrier frequency giving a good curative effect lies within the range of 10 to 15 kHz. For treating certain diseases it is proposed to use not one frequency, but a combination of consecutively changing frequencies producing different effect.

For example:

Arthrites—arthroses—1.2+1.6+9.2+9.6 Hz;

Bronchial asthma—0.9+4+8.0+9.45 Hz;

Depressions—5.8+9.6 Hz;

Impotency—2.6+4.0+9.4 Hz;

Climax—4.0+4.9 Hz (regulation of the function of the hypophysis and ovaries);

Urothiliasis—2.8+3.3+8.1 Hz (regulation of the function of renal glomeruli and tubules);

Angina—35+71.5+87+20.5+75.5++82+86+89 Hz;

Weakening of the cardiac muscle—99.75 Hz.

The low-frequency electromagnetic therapy causes resonance phenomena, but the energy introduced in this case into the organism is so small that the energy information homeostasis is not disturbed, this being of importance, especially for treating oncologic patients.

The accompanying Drawing shows a block diagram of the proposed apparatus for electromagnetic field therapy. The proposed apparatus for electromagnetic field therapy comprises power supply source 1 connected to stabilizer 2, matching unit 3 coupled to antenna 4, block 5 for shaping packets of radio pulses, whose input is connected to the stabilizer 2 and whose output is connected to the matching unit 3. The apparatus further comprises computer interface unit 6, liquid-crystal display 7 intended for displaying the parameters of the treatment program being carried out, and control keyboard 8, connected to the unit 5 for shaping packets of radio pulses, which unit 5 is made as a microprocessor controller with a permanent memory with a capacity for up to 1000 programs of treatment, up to 20 frequencies in each program, each frequency lasting for 1 to 4000 seconds.

The proposed apparatus for electromagnetic field therapy operates in the following manner.

An operator manipulates the control keyboard 8 and switches-on the apparatus. Then the operator keys-in the required treatment program either by using either the keyboard 8 or the computer interface unit 6 (the computer is not shown in the Drawing). The program can comprise one or more frequencies in the range of from 0.1 to 100 Hz. For each frequency an operation time is preset within a range of 1 to 4000 seconds. The microprocessor controller memorizes the entered program. The microprocessor controller can memorize and store from 1 to 1000 programs. Then the antenna 4 is directed to the region of projection of the organ of interest, to the patient's chest or back, and the performance of the treatment program is started. The microprocessor controller, performing the prescribed program, shapes packets of audio-frequency filled pulses in the range of 0.1 to 100 Hz. These packets of pulses are fed to the matching unit 3 and via it to the antenna 4. The operating mode of the microprocessor controller pops up on the liquid crystal display 7. On completion of the prescribed program the apparatus switches off automatically. The treatment is based on resonance phenomena, and not on making the organs perform functions not indigenous to them. This is exactly the reason why apparatus intended for field electromagnetic therapy cannot bring about overdosage or cause aggravation of diseases. If the introduced frequency induces a resonance, the organism is in need of this frequency, and a curative effect is present. If there is no resonance, there is no curative effect either. As a consequence, this apparatus can do no harm.

In the apparatus of the present invention commonly known instruments are used. For instance, a Microchip Technology Inc. controller (1997 Technical Library Second Edition CD-ROM) can be used as the microprocessor controller; an Analog Devices Inc. computer interface (1996 Designer's Reference Manual, pp. 19–13) can be used as the interface unit 6; and a Holtec HT 1613 display (Patent No. 84545 (R.O.C.) pending: Ser. No. 08/214,079 (USA)) can be used as the liquid crystal display 7.

A portable apparatus of the invention is intended for treating diseases and eliminating pathological states, and it can be used in seven different operation modes. A high therapeutic effect is attained owing to the high frequency setting with taking into account individual peculiarities of a human patient. A physician diagnoses the patient's state and programs the apparatus for treating seven of the 626 known diseases and symptoms, compiling individualized prescriptions for each. The apparatus operates further without the physician's participation: the user himself switches on the required mode. The patient can perform physician's functions himself, if he is sure that the diagnosis is precise. It is reasonable to do that, if the disease is common cold, intoxication (including alcohol intoxication, for removing the hangover syndrome), eye fatigue, allergy, and the like.

The present method has passed clinical tests at P.V. Mandryk Central Military Clinical Hospital, at the State Preventive Medicine Research Center, at Academician Sechenow Moscow Medical Academy, in the Department of Radiation Medicine of Moscow Diagnostics and Surgery Research Institute of the Ministry of Health of the Russian Federation, at the "Ultramed" Research Center (Moscow). The method of electromagnetic field therapy according to the present invention will be better understood from examples presented hereinbelow by way of illustration.

EXAMPLE 1

Female patient V. from the town of Zelenograd complained of varicous dilation of veins. Many years of laser therapy, chemotherapy, and other treatments gave no success. The patient's legs were swollen, with ulcers down to 8 cm deep.

The patient was treated by the method of electromagnetic therapy according to the invention. The patient was acted upon with a pulsed electromagnetic field having an intensity of 0.1 V/m$^2$ without changing the energy-information homeostasis. The carrier frequency was 10 kHz. The action was effected locally onto the legs. The program comprised the following frequencies: 10 Hz during 600 s, 33.5 Hz during 300 s, 94 Hz during 300 s, 85 Hz during 300 s, 46.5 Hz during 300 s, 99.5 Hz during 300 s. The treatment was carried out once a day before going to bed, and after the seance the patient used to go to bed without getting up. During a period of two weeks the swelling went down, the ulcers cicatrized, and the patient could put her boots on. No recurrence of the disease was observed during three years.

EXAMPLE 2

Male patient I., aged 65, from the town of Voronezh, complained of bronchial asthma. He suffered many years from aggravations occurring every spring and autumn during the periods of rain and raw weather. The patient was treated by the method of electromagnetic field therapy according to the invention: he was acted upon with a pulsed electromagnetic field having an intensity of 0.1 V/M$^2$ without changing the energy-information homeostasis with a preset radio pulse packet repetition frequency with spacing of 0.01 Hz. The carrier frequency was 12 kHz. The whole organism was acted upon. The program comprised the following frequencies: 0.9 Hz during 300 s, 4.0 Hz during 300 s, 8.0 Hz during 300 s, 9.45 Hz during 300 s, 82 Hz during 300 s, 82 Hz during 300 s. The first séance was carried out at 5 p.m. in April. The séance was repeated next morning and three more séances were carried out during the day. Toward the evening the aggravation ceased and no recurrence was registered in autumn.

EXAMPLE 3

Male patient K., aged 55, from the town of Zelenograd, complained of hypertension. The patient used to take medicines for normalizing the blood pressure. The patient was treated with selected individual regulation frequencies. After that the patient always carried an apparatus about him. As soon as the blood pressure starts to rise, he actuates the program, and the pressure normalizes. It has been three years and a half since the patient stopped taking any tablets and feels well.

The patient was treated in accordance with the proposed method of electromagnetic field therapy. The patient was acted upon with a pulsed electromagnetic field having an intensity of 0.1 V/m$^2$ without changing the energy-information homeostasis with a preset radio pulse packet repetition frequency with spacing of 0.01 Hz. The carrier frequency was 12 kHz. The whole organism was acted upon. The program comprised the following frequencies: 3.3 Hz during 300 s, 6.0 Hz during 300 s, 9.2 Hz during 300 s, 9.4 Hz during 300 s, 9.5 Hz during 300 s, 62.5 Hz during 300 s.

The present method can be successfully used for treating prostatitis. A set of programs was developed for treating prostatitis, which comprises the following programs:

1. Prostate: 2.6+4.0+4.9+9.4+19.5+51+51.5++57 Hz, each frequency lasting for 300 s.
2. Regulation of the functions of the hypthalamus-hypophysis-adrenal glands-sexual glands system: 4.0+4.9++5.5+9.4 Hz, each frequency lasting for 300 s.
3. Energy program: 10+12.5+19 Hz, each frequency lasting for 300 s.
4. Arthritis—arthrosis: 1.2+1.6+9.2+9.6+95.5+96.5 Hz, each frequency lasting for 300 s.
5. Testicle, testis: 14+4.5+51 Hz, each frequency lasting for 300 s.
6. Disturbance of drive:4.5+14+15.5+55+55.5++57+49.5 Hz, each frequency lasting for 300s.
7. Disturbance of local circulation: 50+58+85.5Hz, each frequency lasting for 300 s.

This set of programs has been successfully tested at the medical center "Andromed" (Voronezh). 135 patients with similar problems were treated during the period ofg six months. The experiment has shown 85% of cure.

So, the present method of and apparatus for electromagnetic field therapy with such an embodiment thereof made it possible to provide harmonization of the functioning of human organs and systems owing to resonance phenomena induced in the organism by prescribed frequencies and thereby to broaden the possibilities of their use and to automate the process of treatment.

INDUSTRIAL APPLICABILITY

The present invention can be used for acting upon the human organism with a weak low-frequency modulated electromagnetic field for treating various diseases, for harmonizing the functioning of the organs and enhancing the protective forces of the organism.

What is claimed is:

1. A method for electromagnetic field therapy for a mammal comprising applying to said mammal a pulsed electromagnetic field in the form of a first radio pulse packet having an intensity of about 0.1V/m$^2$ over a frequency range of 0.2 Hz to 10 Hz with a spacing of 0.01 Hz followed by a second radio pulse packet having an intensity of about 0.1 V/m$^2$ over a frequency range of 10 to 100 Hz with a spacing of about 0.1 to 0.2 Hz, both packets having a carrier frequency of from about 10 kHz to about 15 kHz.

2. A method of electromagnetic field therapy according to claim 1, characterized in that the action on the human organism with a pulsed electromagnetic field is performed locally through the projection zone of its organ.

3. A method of field electromagnetic field therapy according to claim 1, characterized in that the action with a pulsed electromagnetic filed is performed on the whole organism.

4. A method for electromagnetic field therapy according to claim 1 which does not change the energy information homeostasis of said mammal.

5. A method for electromagnetic field therapy according to claim 1 wherein said mammal is a human.

* * * * *